United States Patent
John (10) Patent No.: US 9,549,957 B2
(45) Date of Patent: Jan. 24, 2017

(54) ACTIVE AGENT COMPLEX AND FORMULATION COMPRISING THE ACTIVE AGENT COMPLEX

(75) Inventor: Sabrina John, Berlin (DE)

(73) Assignee: Chemisches Laboratorium, Dr. Kurt Richter, GMBH, Berlin (DE)

(*) Notice: Subject to any disclaimer, the term of this patent is extended or adjusted under 35 U.S.C. 154(b) by 457 days.

(21) Appl. No.: 13/358,369

(22) Filed: Jan. 25, 2012

(65) Prior Publication Data

US 2012/0189651 A1  Jul. 26, 2012

Related U.S. Application Data

(63) Continuation-in-part of application No. PCT/EP2010/059238, filed on Jun. 29, 2010.

(30) Foreign Application Priority Data

Apr. 12, 2010  (DE) .................. 10 2010 014 666

(51) Int. Cl.
*A61K 36/076* (2006.01)
*A61K 36/899* (2006.01)
*A61K 9/00* (2006.01)

(52) U.S. Cl.
CPC .......... *A61K 36/076* (2013.01); *A61K 36/899* (2013.01); *A61K 9/0014* (2013.01)

(58) Field of Classification Search
None
See application file for complete search history.

(56) References Cited

FOREIGN PATENT DOCUMENTS

| CN | 1899543 A | * | 1/2007 |
| CN | 101264253 A | * | 9/2008 |
| DE | 101 51 649 | | 5/2003 |
| KR | 2008105808 A | * | 12/2008 |
| WO | WO 00/64279 | | 11/2000 |
| WO | WO 2006/123887 A1 | * | 11/2006 |

OTHER PUBLICATIONS

Khare, C.P. ed. (Indian Medicinal Plants: An Illustrated Dictionary. Boston: Springer Science, 2007. pp. 480).*
Zuo (CN 1899543 A (English translation))—Jan. 2007.*
Shinn (Natural Foods Merchandiser (Mar. 2009) vol. 30.3 p. 84).*
PCT Search Report for International Application No. PCT/EP2010/059238, mailed on Apr. 12, 2010.
CLR Newsletter Sep. 2009; Chemisches Laboratorium, Dr. Kurt Richter GmbH.
SyriCalm™ CLR; CLR Chemisches Laboratorium, Dr. Kurt Richter GmbH, 2010.
"Exhibition of Innovation", Personal Care Magazine, 2010 (http://www.personalcaremagazine.com/Story.aspx?Story=6377).

* cited by examiner

*Primary Examiner* — Susan Hoffman
(74) *Attorney, Agent, or Firm* — Kagan Binder, PLLC (57) ABSTRACT

The present invention relates to an active agent complex of extracts of *Poria cocos* and a species of the genus *Phragmites*, in particular *Phragmites kharka* (also *Phragmites karka*), formulations comprising said active agent complex as well as to the use of the formulations of the invention for the strengthening, maintenance and quicker restoration of epidermal integrity.

12 Claims, 8 Drawing Sheets

Interleukin-8 expression after hyperosmotic stress

ACTIVE AGENT COMPLEX AND FORMULATION COMPRISING THE ACTIVE AGENT COMPLEX

This is a continuation-in-part of International Application PCT/EP2010/059238, with an international filing date of Jun. 29, 2010, which in turn claims priority to German National Patent DE 10 2010 014 666.8, with a filing date of Apr. 12, 2010, the contents of which are incorporated herein by reference.

The present invention relates to an active agent complex of extracts of *Poria cocos* and a species of the genus *Phragmites*, in particular selected from *Phragmites australis* (Cay.) Trin. ex Steud., *Phragmites communis* Trin., *Phragmites karka* (Retz.) Trin. ex Steud., *Phragmites longivalvis* Steud., *Phragmites roxburghii* Steud., *Phragmites vulgaris* (Lam.) Crep., in particular *Phragmites kharka* (also *Phragmites karka*), formulations comprising said active agent complex as well as to the use of the formulations of the invention for the strengthening, maintenance and quicker restoration of epidermal integrity.

The species *Phragmites australis* (Cay.) Trin. ex Steud. is also known to the person skilled in the art as *Arundo phragmites* L., *Arundo vulgaris* Lam., *Phragmites communis* Trin., *Phragmites longivalvis* Steud., *Phragmites vulgaris* (Lam.) Crep.

The species *Phragmites communis* Trin. is also known to the person skilled in the art as *Arundo phragmites* L., *Arundo vulgaris* Lam., *Phragmites australis* (Cav.) Trin. ex Steud., *Phragmites longivalvis* Steud., *Phragmites vulgaris* (Lam.) Crep.

The species *Phragmites karka* (Retz.) Trin. ex Steud. is also known to the person skilled in the art as *Arundo karka* Retz., *Phragmites roxburghii* Steud.

The species *Phragmites longivalvis* Steud. is also known to the person skilled in the art as *Arundo phragmites* L., *Arundo vulgaris* Lam., *Phragmites australis* (Cav.) Trin. ex Steud., *Phragmites communis* Trin., *Phragmites vulgaris* (Lam.) Crep., *Hakonechloa macra* (Munro) Makino.

A further preferred species of the *Phragmites* genus to be used in accordance with the present invention is *Phragmites communis* or *Phragmites australis*.

*Poria cocos* is a solid fungus (Polyporaceae) which is also known as Fu Ling, Tuckahoe, Indian Bread or Hoelen. It grows preferably on pine roots where it is harvested between July and October and has a very hard white mycelium which lead to its name. *Poria cocos* has been used in diverse ways in Traditional Chinese Medicine (TCM) and other schools of Far Eastern Medicine for a long time. It is said to have immunological, anti-inflammatory and anti-tumour effects. Traditionally, it is also used for the treatment of insomnia, as diuretic, for the balance of electrolytes, for "invigorating" the spleen and as tonic for the internal organs. It is also referred to as "medicine or mushroom of immortality".

*Phragmites*, such as *Phragmites kharka*, belongs to the true grasses (*Poaceae*) and is generally referred to as reed. It is a tall grass growing in wetlands which is native in all tropical regions of the earth and it has been used in various manners. e.g., for thatching and for the purification of water. its pharmacological properties have been known for a long time. Thus, *Phragmites kharka* is used in traditional medicine for the treatment of fever, cough and even of cancer. The North American Navajo Indians used *Phragmites* for the treatment of skin diseases.

Preparation of the Active Agent Complex

The active agent complex of the invention comprises a combination of the extracts of *Poria cocos* and a species of the genus *Phragmites*, selected from, *Phragmites australis* (Cay.) Trin. ex Steud., *Phragmites communis* Trin., *Phragmites karka* (Retz.) Trin. ex Steud., *Phragmites longivalvis* Steud., *Phragmites roxburghii* Steud., *Phragmites vulgaris* (Lam.) Crep., in particular *Phragmites kharka*, wherein the extracts comprise aqueous, glycolic or alcoholic extracts. In this context, the extraction with water or buffers such as PBS (phosphate-buffered saline) or Sorensen's buffer is preferred.

The extraction should take place at a pH of 2 to 9, preferably at a pH of 4.5, and at a temperature between 40° C. and 100° C., preferably at 80° C. The extraction can be carried out for 1 to 24 hours, preferably for 2 to 4 hours.

According to the invention, the extract of *Poria cocos* and the extract of a species of the genus *Phragmites*, in particular *Phragmites kharka*, can be produced by combined or separate extraction.

Preferably, the extract produced by combined extraction or the extracts produced by separate extraction, subsequent to their combination, are subjected to purification/separation by centrifugation, decantation, filtration and/or particularly preferred by ultrafiltration (preferably with a cut-off of 100 kDa). The extracts may preferably be subjected to conjoint maturation which lasts preferably between 2 to 10 days, more preferably 4 days.

In a particularly preferred embodiment *Poria cocos* and a species of the genus *Phragmites*, in particular *Phragmites kharka*, are subjected to separate extraction under the above conditions, the resulting extracts are combined and then subjected to separation as described above, in particular by ultrafiltration (cut-off of 100 kDa).

For the component *Poria cocos*, the whole fungus is used for the extraction, also with respect to the component *Phragmites kharka* the entire plant, i.e. with rhizome and leaves or only the rhizome or the leaves, is used as starting material for the extraction. In this context, the plant material can be fresh, dried or freeze-dried.

The relation between plant material and extraction agent is preferably 1 to 10% (w/w) and particularly preferred 2 to 5% (w/w).

Summary of the preparation of the active agent complex
aqueous extraction in water, glycolic solution, buffer (PBS, Sorensen)
pH between 2 to 9, preferably 4.5
duration of extraction: 1 to 24 h, preferably 2 to 4 h
temperature: 40 to 100° C., preferably 80° C.
preferably separate extraction of the components
preferably separation by ultrafiltration (100 kDa)

In a further embodiment, the present invention provides formulations which comprise the active agent complex of the invention.

Preferably, the formulations of the invention are in form of formulations for topical application onto the skin in form of a cream (o/w or w/o), an ointment, a paste, lotion (o/w and w/o emulsion), multiple emulsion (w/o/w or o/w/o), a solution (oily, alcoholic or aqueous), a dispersion (hydrodispersion or lipodispersion), a stick, foam or gel.

The formulations of the invention can be formulated in a manner which per se is known to the person skilled in the art with the common agents and excipients, as described e.g. in Bauer et al., Pharmazeutische Technologie, 5$^{th}$ ed., Govi-Verlag Frankfurt, 1997; Rudolf Voigt, Pharmazeutische Technologie, 9$^{th}$ ed. Deutscher Apotheker Verlag Stuttgart, 2000.

The formulations of the invention contain between 1% (w/w) to 10% (w/w), more preferred 2% (w/w) to 5% (w/w)

and particularly preferred between 3% (w/w) of the active agent complex of the invention.

According to the present invention, the active agent complex of the invention can also be combined in combination with further plant extracts or active agents having an anti-inflammatory effect or an effect protecting or restoring the skin barrier.

The present invention further relates to the use of the formulations of the invention for the maintenance of the barrier function of the epidermis as well as in the therapy and prophylaxis of skin conditions requiring the strengthening and/or maintenance of the epidermal barrier and anti-inflammatory care and of skin conditions involving skin barrier dysfunction. Thus, the present invention in particular relates to formulations for topic use with skin conditions requiring the strengthening and/or maintenance of the epidermal barrier and anti-inflammatory care, such as:

atopic skin (neurodermitis [atopic dermatitis], atopic eczema, endogenous eczema),
  psoriasis
  ichthyosis,
  general dry skin conditions (xerodermia), for example caused by
    general skin ageing,
    hormonal as well as pathological alternations, such as diabetes,
    exogenous influences such as daily hygiene and the exposition to water, sindets, soap, chemicals, cosmetics, disinfectants etc. associated therewith,
    climatic conditions (UV, dry air, sea water etc.), as well as
    side effects of medicaments.

The invention comprises further the use of the formulation for the treatment of inflammatory processes of the skin, in particular with allergic reactions, phototoxic reactions, sunburn and actinic keratosis, inflammations of the scalp (pityriasis simplex capitis, pityriasis oleosa), seborrheic dermatitis, rosacea and with processes inducing histamine release such as insect stings or bites and pruritus.

Only an intact skin barrier protects against excessive transepidermal loss of water and, thus, contributes to the resistance of the skin to irritant agents.

Damage of the epidermal barrier may result in elevated values of transepidermal water loss (TEWL-values), inflammatory reactions and an increased penetration of exogenous substances and/or organisms which cause the inflammatory process (release of free radicals or endotoxins).

Moreover, basal keratinocytes express pro-inflammatory cytokines which lead to further cell damage and, thus, further impair the epidermal barrier.

Thus, the aim of the present invention is to provide a product which strengthens the epidermis and at the same time has an anti-inflammatory effect and which contributes to the resilience of the skin and, thus, avoids or minimises the mentioned conditions resulting from stressed skin.

The application of the formulations of the invention results inter alia in improved skin complexion as well as in a reduced TEWL value.

The TEWL value refers to the amount of water which is diffused via the stratum corneum of the skin per hour and $cm^2$. Thus, changes in the transepidermal water loss provide information on the efficacy of the skin barrier function.

Furthermore, after application of the formulations according to the invention, skin irritations, erythemas and pruritus were reduced.

Moreover, increased tolerance of the skin towards UV radiation and other exogenous stress factors such as osmotic stress and photoallergic reactions are achieved in vitro.

In vivo tests prove that the active agent complex has an advantageous effect on epidermal cells which were exposed to UV light. Furthermore, in vitro, it reduces the loss of energy and viability of the cells to a high degree and efficiently down-regulates the production of pro-inflammatory cytokines. In this context, the active agent complex of the invention showed significantly accelerated reduction of inflammatory erythemas caused by UV radiation. Further, the active agent complex in vivo showed a significantly increased effect even in comparison to the positive control containing the antihistamine dimetindene maleate.

It was shown that the active agent complex of the invention is capable of compensating the phototoxic effects of hypericin, a known photoallergen, on cell viability. After treatment with hypericin and UV radiation, the active agent complex of the invention reduces the production of TNF-α and IL-8, two of the most important pro-inflammatory mediators which are known to cause skin irritations.

There is both in vitro and in vivo evidence, that the active agent complex has a significant effect on epidermal homeostasis and the epidermal barrier function. In in vivo studies the active agent complex of the invention shows even better results than the positive control, the potent anti-inflammatory pharmaceutical 5% panthenole in lanolin.

It was further observed that the active agent complex of the invention has a positive effect in keratinocytes which were exposed to osmotic stress by intense down-regulation of the production of pro-inflammatory mediators.

As illustrated in FIGS. 1 to 7, the active agent complex of the invention consisting of two components shows a super-additive effect with respect to the strengthening, maintenance and quicker restoration of epidermal integrity.

Thus, it could be shown that the active agent complex of the invention in vitro has an effect on the following parameters of the cells after UV radiation:

In Vitro Experiments

In all the tests described and in FIGS. 1 to 7, R1=*Phragmites kharka* extract, R2=*Poria cocos* extract and R3=active agent complex of *Phragmites kharka* and *Poria cocos* according to the invention, cells that were treated only with medium served as controls.

1. Reduction of UV-Induced TN-Alpha Expression (TNF-Alpha Assay)

UV light and other factors that can trigger a cutaneous inflammation lead to the expression of TNF-alpha (tumour necrosis factor), the most important pro-inflammatory cytokine. TNF-alpha controls both local and systemic inflammatory processes by induction of cyclooxygenase-2 (COX-2) and prostaglandin E2 (PGE2). This induces the expression of substance P (SP), a sensory neuropeptide which is responsible for the sensation of pain and, moreover, stimulates TNF-alpha again. This illustrates the necessity to inhibit or minimise TNF-alpha, which is at the basis of the cytokine cascade, during an inflammatory process.

Apart from the sensory pain sensation, the consequences of a dermal inflammation, however, are reddening and swelling, which weakens the barrier function of the skin. With UV-induced cutaneous erythema, there is also damage to the DNS induced directly by UVB radiation, which, on the one hand leads to TNF-alpha expression and, on the other hand, also increases the number of apoptotic cells. This, in turn, can lead to a drastic impairment of the differentiation process of the keratinocytes and, thus, to an impaired formation of the Stratum corneum.

Due to its ability to protect the epidermal homeostasis from such influences in an effective manner in combination with its very good tolerability, the active agent complex according to the invention is ideally suited to strengthen, maintain and restore the epidermal integrity.

TNF-Alpha After UV Radiation—Procedure

Human keratinocytes were incubated at 37° C. and 5% $CO_2$ in Dulbecco's Modified Eagle Medium (DMEM); Biochrom, F0415) which was supplemented with 5% FCS (Foetal Calf Serum; Biochrom, S 0115—heat-inactivated) and L-glutamine (Biochrom, K 0282).

Prior to reaching the stationary growth phase, the cells were trypsinated, which included pretreatment with an EDTA solution (ethylene diamine tetra-acetic acid, Biochrom, L2113, 1:20 in PBS). After determination of the number of cells, a cell suspension was prepared and seeded into a 96 well microtitre plate (MTP; TPP, 92696) with a cell number of $3 \times 10^4$ cells/well.

The samples to be examined, R1-R3, were diluted in medium and added to the cells at the corresponding concentrations. The plates were incubated for 72 h at 37° C. and 5% $CO_2$.

After expiry of this time period, the medium was removed and the cells were washed with PBS (phosphate-buffered saline solution, without $Mg^{2+}$ and $Ca^{2+}$; Biochrom, L1825).

For the subsequent UV radiation, the cells were covered with 50 µl PBS/well and radiated with 2 $J/cm^2$ UVA+0.2 $J/cm^2$ UVB by means of a UV lamp simulating the natural sun light spectrum (Dr. Hönle, SOL 500).

After repeated incubation of the cells at 37° C. and 5% $CO_2$ for 18 h, the TNF-alpha luminescence ELISA was carried out (R&D Systems, QTA00B).

The microtitre plates were centrifuged at 250×g for 10 minutes and the media supernatants were carefully transferred to the microtitre plate coated with anti-TNF-alpha+ assay diluent, without taking up the precipitated cell debris. The cell supernatants to be examined were incubated for 3 h at room temperature while shaking. Then, the plates were incubated with the $2^{nd}$ antibody (anti-TNF-alpha-POD) for 2 h at room temperature on the shaker. After addition of the Glo-reagent, a ten-minute incubation of the plate, protected from light, took place at room temperature.

Luminescence was measured in a microplate reader (Labsystems, Fluoscan Ascent Fla.). The obtained RLU values (Relative Luminescence Units) correspond to the amount of the expressed TNF-alpha. Cells which had not been pretreated with R1, R2, R3 served as controls. The RLU values of these control cells were set as 100% value.

Figure 1:
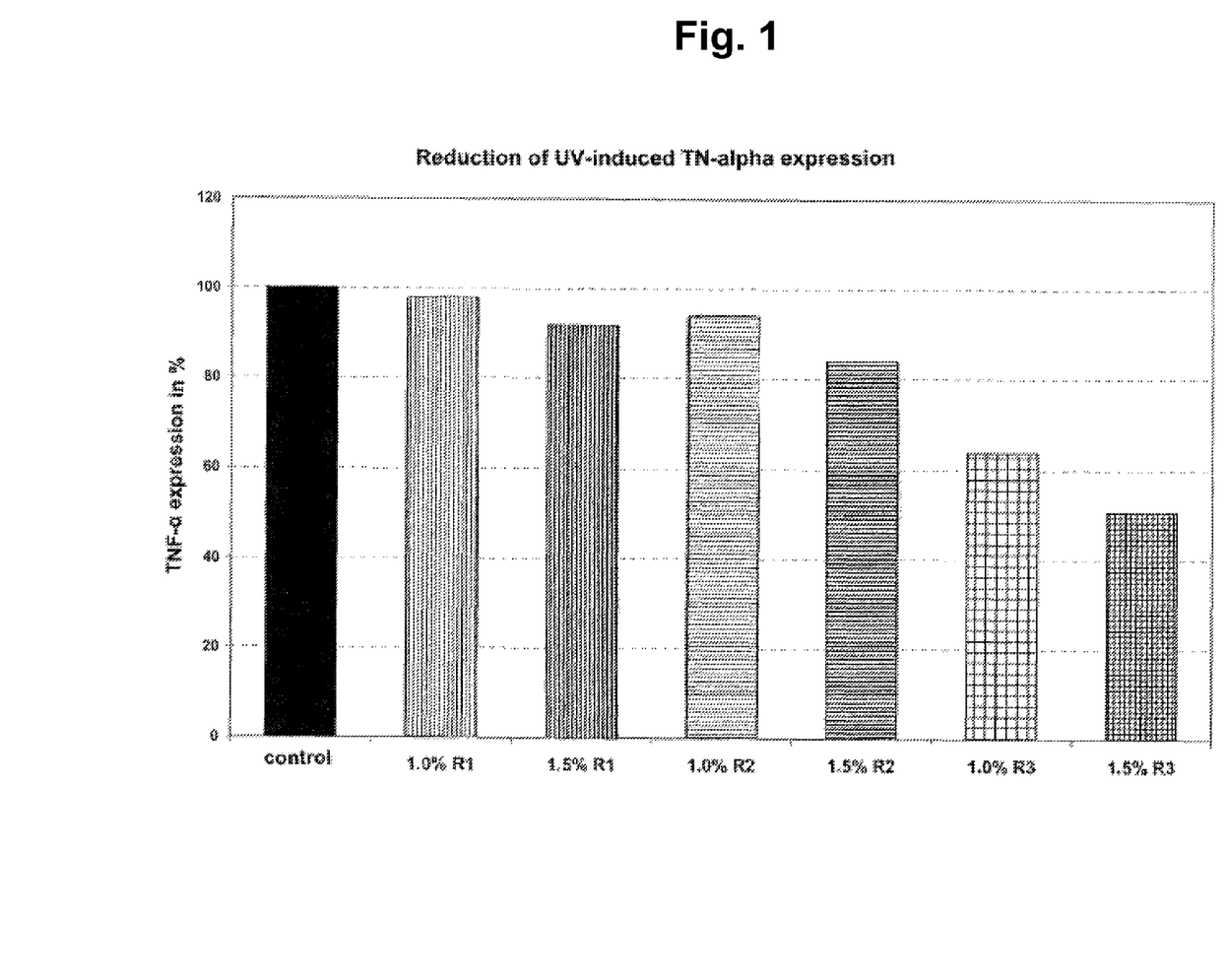
FIG. 1 showing the graphical presentation of a reduction of TNF-alpha (Tumore necrose factor) expression in human keratinocytes, pretreated with various active agent complexes, following ultraviolet radiation treatment.

As illustrated in FIG. 1, the active agent complex according to the invention (R3) had a significant reducing effect on TNF-alpha, which was dose-dependent, whereas the individual components caused only an insignificant reduction, if at all.

2. Reduction of UV-Induced IL-8 Expression

Interleukin-8 is one of the primary inflammatory cytokines stimulated mainly by TNF-alpha and interleukin-1, which, in turn, is expressed by exogenous factors such as UV, infections, ischemia, wound healing after traumata, phototoxic and photoallergic reactions, respectively, osmotic stress and others by a plurality of cell types. It plays a crucial role in immune-related inflammations where it activates neutrophils and leads them to the source of the inflammation where they trigger intensification of the chemotactic recruitment of the neutrophils by IL-8 secretion. Thus, it is a key cytokine for inflammatory processes, which can lead to chronic inflammatory conditions in the case of lack of intervention.

Interleukin-8 After UV Radiation—Procedure

Human keratinocytes were incubated at 37° C. and 5% $CO_2$ in Dulbecco's Modified Eagle Medium (DMEM); Biochrom, F0415) which was supplemented with 5% FCS (Foetal Calf Serum; Biochrom, S 0115—heat-inactivated) and L-glutamine (Biochrom, K 0282).

Prior to reaching the stationary growth phase, the cells were trypsinated, which included pretreatment with an EDTA solution (ethylene diamine tetra-acetic acid, Biochrom, L2113, 1:20 in PBS). After determination of the number of cells, a cell suspension was prepared and seeded into a 96 well microtitre plate (MTP; TPP, 92696) with a cell number of $3 \times 10^4$ cells/well.

The samples to be examined, R1-R3, were diluted in medium and added to the cells at the corresponding concentrations. The plates were incubated for 72 h at 37° C. and 5% $CO_2$.

After expiry of this time period, the medium was removed and the cells were washed with PBS (phosphate-buffered saline solution, without $Mg^{2+}$ and $Ca^{2+}$; Biochrom, L1825).

For the subsequent UV radiation, the cells were covered with 50 μl PBS/well and radiated with 2 $J/cm^2$ UVA+0.2 $J/cm^2$ UVB by means of a UV lamp simulating the natural sun light spectrum (Dr. Hönle, SOL 500).

After further incubation of the cells at 37° C. and 5% $CO_2$ for 18 h, the interleukin-8 luminescence ELISA was carried out (R&D Systems, Q8000B).

The microtitre plates were centrifuged at 250×g for 10 minutes and the media supernatants were carefully transferred to the microtitre plate coated with anti-IL-8+ assay diluent, without taking up the precipitated cell debris. The cell supernatants to be examined were incubated for 2 h at room temperature while shaking. Then, the plates were incubated with the $2^{nd}$ antibody (anti-IL-8-POD) for 3 h at room temperature on the shaker. After addition of the Glo-reagent, a ten-minute incubation of the plate, protected from light, took place at room temperature.

Luminescence was measured in a microplate reader (Labsystems, Fluoscan Ascent Fla.). The obtained RLU values (Relative Luminescence Units) correspond to the amount of the expressed Interleukin-8. Cells which were not pretreated with R1, R2, R3 serve as controls. The RLU values of these control cells were set as 100% value.

Figure 2:
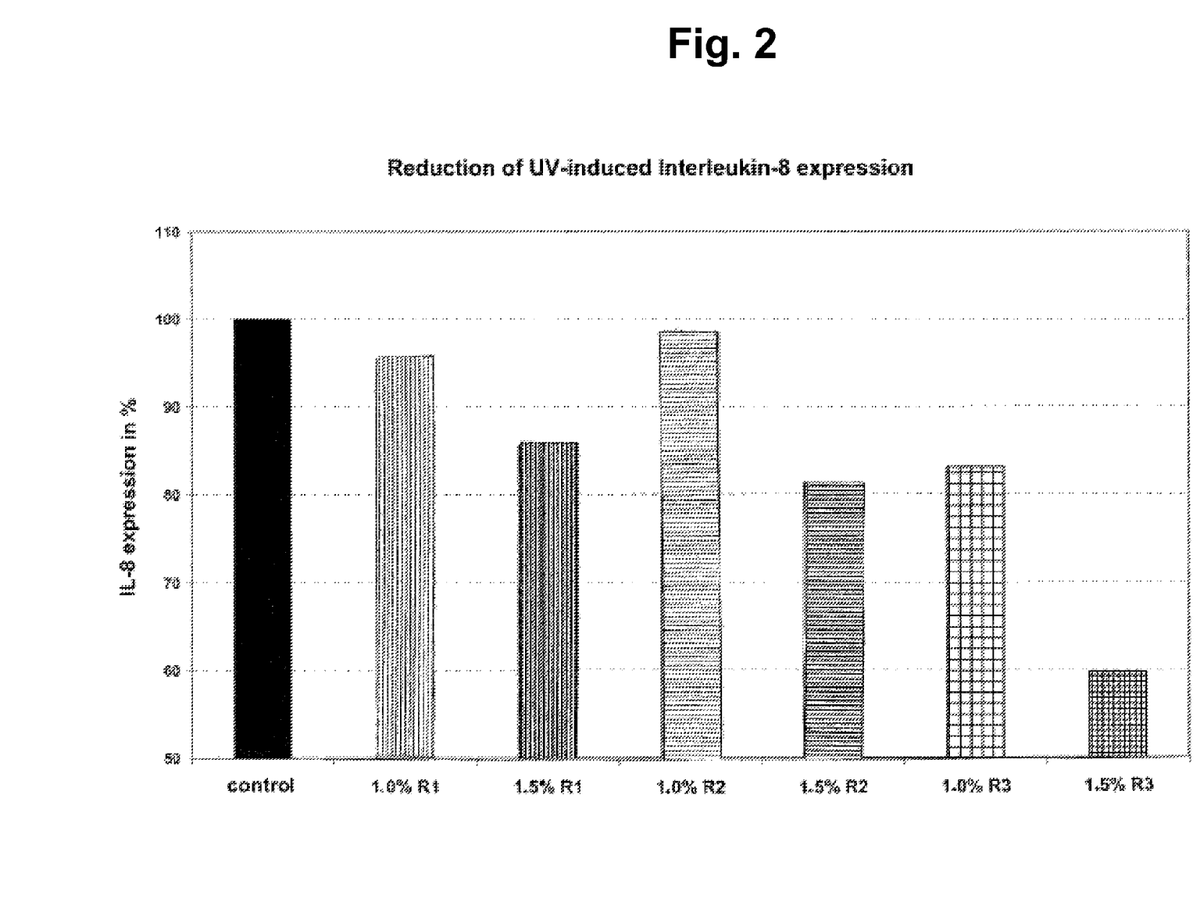
FIG. 2 showing the graphical presentation of a reduction of Interleukin-8 expression in human keratinocytes, pretreated with various active agent complexes, following ultraviolet radiation treatment.
Figure 3:
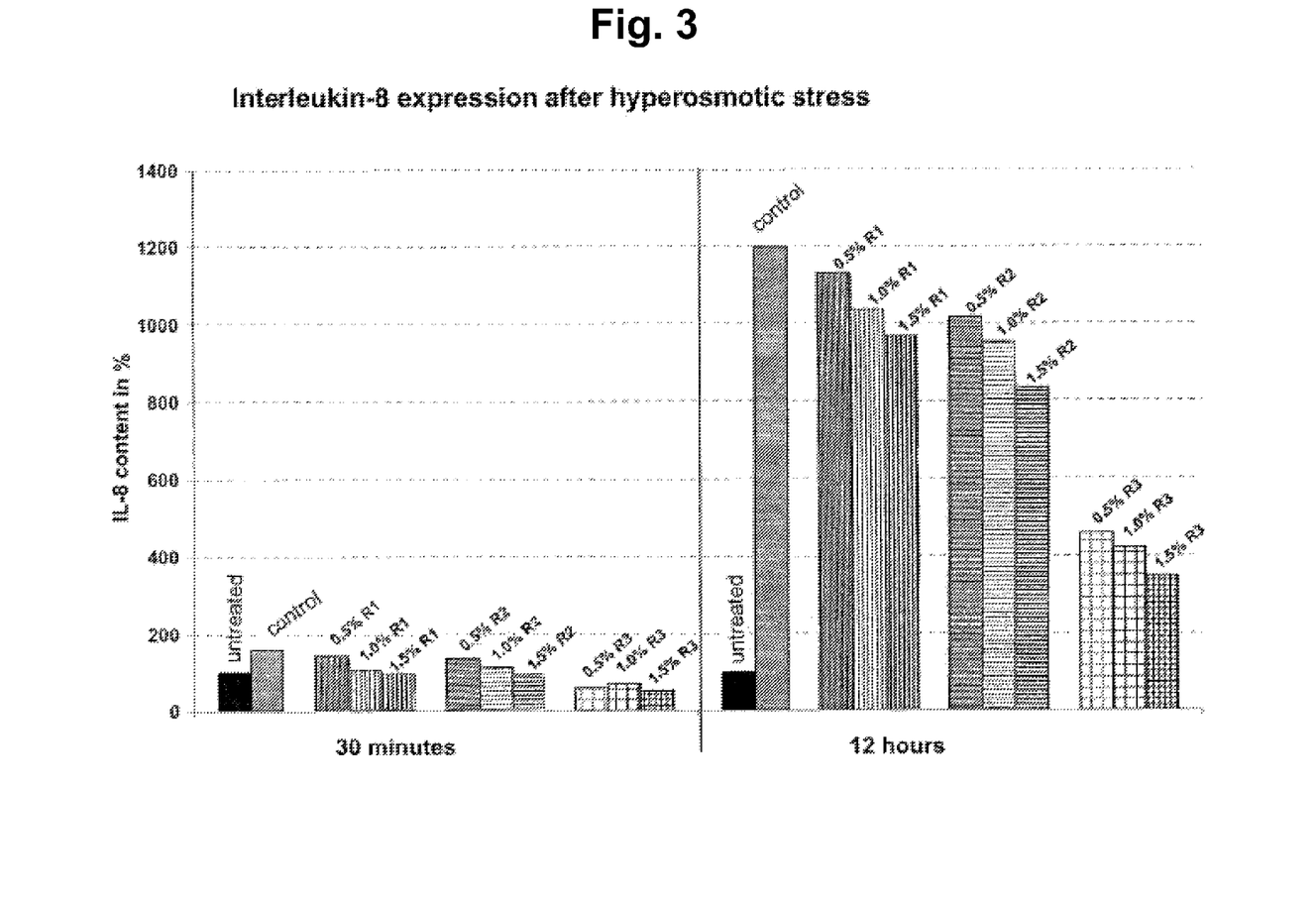
FIG. 3 showing the graphical presentation of an expression of Interleukin-8 in human keratinocytes, pretreated with various active agent complexes, following hyperosmotic stress (400 mOsm) at different time points (30 min and 12 hours) after osmotic treatment.
Figure 4:
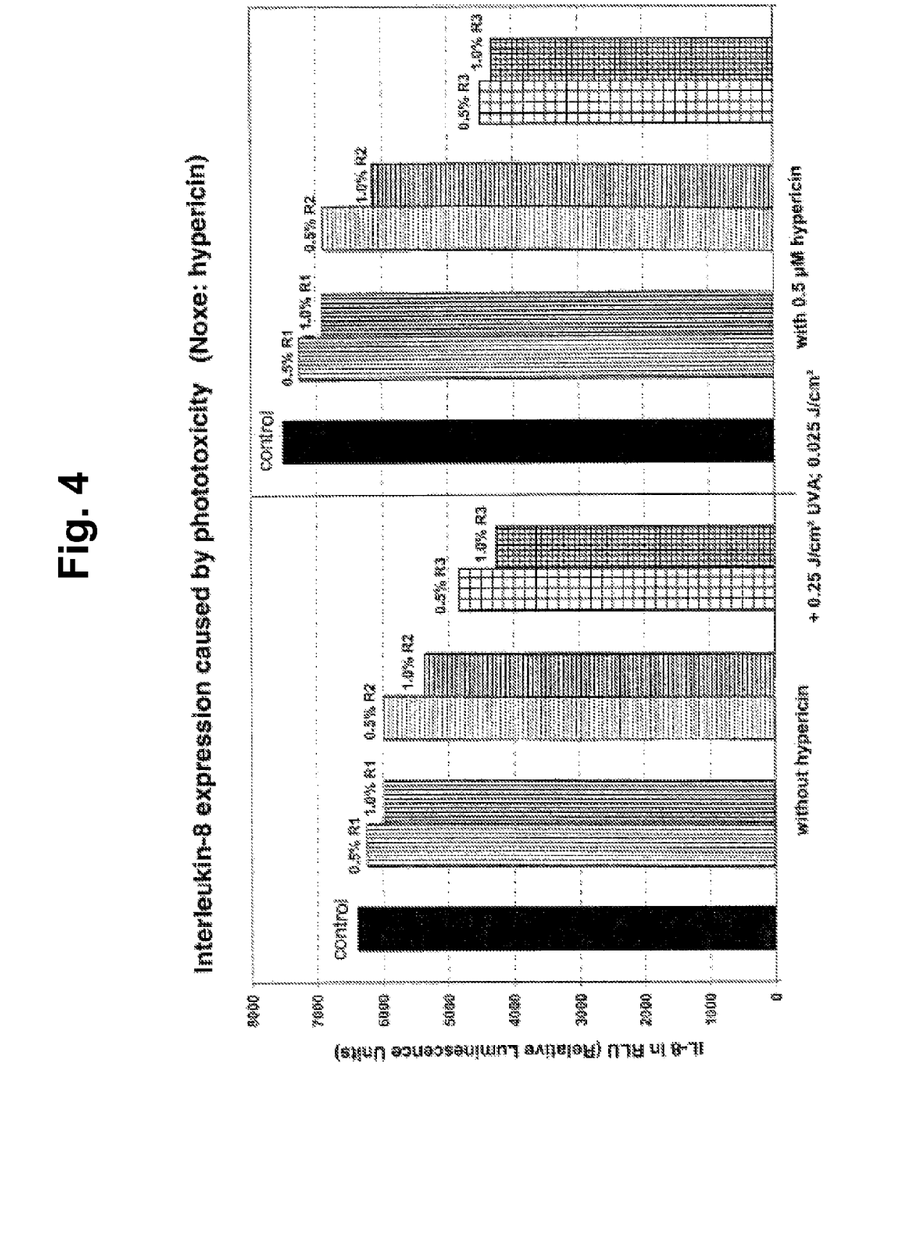
FIG. 4 showing the graphical presentation of an expression of Interleukin-8 expression in human keratinocytes, pretreated with various active agent complexes, following Hypericin and ultraviolet radiation treatment.

The active agent complex according to the invention (R3) reduced the expression of interleukin-8 in a significant and dose-dependent manner and to a much larger extent than the individual components of the active agent complex (see also FIG. 2).

3. Reduction of IL-8 Expression After Hyperosmotic Stress

In the case of hyperosmotic cell stress, the inflammation process takes also place via the activation of the mitogen-activated protein kinases (MAPKs) which includes ERK (extracellular signal-regulated kinase) and c-Jun N-terminal kinase (JNK). These activated kinases induce nuclear transcription factors (NF-kappa B, AP-1) to secrete pro-inflammatory mediators.

Cell damages at DNS level which are caused by inflammatory mechanisms due to osmotic stress are not subject to DNS repair mechanisms as it is the case with UV-induced DNS damages. The possibility of repairing these damages is more limited. Thus, there is a need for an effective active agent which is also capable of preventing or reducing cell damages of this kind.

Interleukin-8 After Hyperosmotic Stress—Procedure

Human keratinocytes were incubated at 37° C. and 5% $CO_2$ in Dulbecco's Modified Eagle Medium (DMEM; Biochrom, F0415) which was supplemented with 5% FCS (fetal calf serum; Biochrom, S0115—heat-inactivated) and L-glutamine (Biochrom, K0282).

Prior to reaching the stationary growth phase, the cells were trypsinated, which included a pretreatment with an EDTA solution (ethylene diamine tetra-acetic acid, Biochrom, L2113; 1:20 in PBS). After determination of the cell number, the cells were suspended and this cell suspension was seeded into a 96-well microtitre plate (MTP; TTP, 92696) with a cell number of $3 \times 10^4$ cells/well.

The samples to be examined R1-R3 were diluted in medium and added to the cells at the corresponding concentrations. The plates were incubated for 72 h at 37° C. and 5% $CO_2$.

After expiry of this time period, the medium was removed and the cells were washed with PBS (phosphate-buffered saline, without $Mg^{2+}$ and $Ca^{2+}$; Biochrom, L1825).

Subsequently, the cells were incubated with different doses of R1-R3 in hyperosmolar medium for 30 min and for 12 h. The hyperosmolar medium was adjusted by means of sodium chloride (Merck, 1064041000) to 400 mOsm using an osmometer (Roebling, Digital Microosmometer Type 5R).

After the incubation periods of the cells at 37° C. and 5% $CO_2$ had elapsed, an interleukin-8 luminescence ELISA (R&D Systems, Q8000B) was carried out.

The microtitre plates were centrifuged at 250×g for 10 minutes and the media supernatants were carefully transferred to the microtitre plate coated with anti-IL-8+ assay diluent, without taking up the precipitated cell debris. The cell supernatants were incubated for 2 hours at room temperature while shaking.

Subsequently, the plates were incubated with the $2^{nd}$ antibody (anti-IL-8-POD) for 3 hours at room temperature on the shaker. After addition of the Glo reagent, a ten-minute incubation of the plate, protected from light, took place at room temperature.

The luminescence was measured in a microplate reader (Labsystems, Fluoscan Ascent Fla.). The obtained RLU values (Relative Luminescence Units) correspond to the content of interleukin-8 expressed. Cells that were not pretreated with R1, R2, R3 serve as control. The RLU values of these control cells were set as 100% value.

Also in these studies, the active agent complex of the invention reduced IL-8 expression significantly and in a dose-dependent manner. The individual components inhibited IL-8 expression to a much smaller degree (see also FIG. 3).

4. Reduction of Phototoxic-Dependent IL-8 Expression

Photoallergic or phototoxic reactions can be triggered by photosensitizing substances. An example is hypericin from *Hypericum perforatum* (St John's wort). The actually damaging components of these substances are free radicals which form under the influence of light. These are the elicitors of the inflammatory condition which is manifest by the expression of the pro-inflammatory cytokines (e.g. IL-8).

Interleukin-8 After Phototoxic Reaction—Procedure

Human keratinocytes were incubated at 37° C. and 5% $CO_2$ in Dulbecco's Modified Eagle Medium (DMEM; Biochrom, F0415) supplemented with 5% FCS (Fetal Calf Serum; Biochrom, S0115—heat-inactivated) and L-glutamine (Biochrome, K0282).

Prior to reaching the stationary growth phase, the cells were trypsinated, which included a pretreatment with an EDTA solution (ethylene diamine tetraacetic acid, Biochrom, L2113; 1:20 in PBS). After determination of the cell number, the cells were suspended and this cell suspension was seeded into a 96-well microtitre plate (MTP; TTP, 92696) with a cell number of $3 \times 10^4$ cells/well.

The samples to be examined R1-R3 were diluted in medium and added to the cells at the corresponding concentrations. The plates were incubated for 72 h at 37° C. and 5% $CO_2$.

After expiry of this time period, the medium was removed and the cells were washed with PBS (phosphate-buffered saline, without $Mg^{2+}$ and $Ca^{2+}$; Biochrom, L1825).

Subsequently, the cells were treated with different doses of R1-R3 in the medium with and without 0.5 µM hypericin (Sigma, 56690). This was followed by UV radiation at 0.25 $J/cm^2$ UVA+0.025 $J/cm^2$ UVB by means of a UV lamp simulating the spectrum of natural sunlight (Dr. Hönle, SOL 500).

After a further incubation of the cells at 37° C. and 5% $CO_2$ for 18 h, the interleukin-8 luminescence ELISA (R&D Systems, Q8000B) was carried out.

The microtitre plates were centrifuged at 250×g for 10 minutes and the media supernatants were carefully transferred to the anti-L-8-coated microtitre plate+assay diluent, without taking up the precipitated cell debris. The supernatants to be examined were incubated for 2 hours at room temperature while shaking. Subsequently, the plates were incubated with the $2^{nd}$ antibody (anti-IL-8-POD) for 3 hours at room temperature on the shaker. After the addition of the Glo reagent, a ten-minute incubation of the plate, protected from light, took place at room temperature.

Luminescence was measured in a microplate reader (Labsystems, Fluorscan Ascent Fla.). The obtained RLU values (Relative Luminescence Units) correspond to the content of interleukin-8 expressed. Cells that were not pretreated with R1, R2, R3 serve as control. The RLU values of these control cells were set as 100% value.

The active agent complex of the invention (R3) also inhibited the phototoxic-dependent expression of interleukin-8 in a dose-dependent manner. The individual components of the active agent complex cause only insignificant inhibition of the expression (see also FIG. 4).

5. Reduction of Formation of Soluble E-Cadherin

Cadherins are calcium-dependant cell-cell adhesion molecules.

Epethelial cadherins (E-cadherins) belong to the group of classical cadherins which are essential for the architecture of the epidermis since they occur in desmosomes as well as in the "adhesion junctions".

E-cadherin functions as the transmembrane anchor which is linked to the actin cytoskeleton of the cell (E-cadherin/catenin complex).

Different mechanisms regulate the adhesion strength of this complex. Thus, a phosphorylation of beta-catenin (induced by MMPs [stromelysine-1, matrilysine]) induces impairment of this complex and, thus, leads to loss of epidermal integrity.

The destruction of the intercellular bond of this complex releases the soluble E-cadherin ectodomain fragment of 80 kDa.

This E-cadherin fragment causes the separation of epithelial cells in vitro and, moreover, contributes to the development of epidermal skin cancers (tumour progression).

The formation of the epidermal layers is an essential property of the dermis. Thus, dysfunctions of the epidermal structure are serious impairments regarding the barrier and protective function of the skin.

As demonstrated in the following, it was surprisingly found that the active agent complex of the invention (R3) has a positive effect on the degradation of the E-cadherin/catenin complex due to damage.

Formation of E-Cadherin Fragment—sE-Cadherin after UV Radiation—Procedure:

Human keratinocytes were incubated at 37° C. and 5% $CO_2$ in Dulbecco's Modified Eagle Medium (DMEM; Biochrom, F0415) which was supplemented with 5% FCS (Fetal Calf Serum); Biochrom, S0115—heat-inactivated) and L-glutamine (Biochrom, K0282).

Prior to reaching the stationary growth phase, the cells were trypsinated which included a pretreatment with an EDTA-solution (ethylene diamine tetra-acetic acid; Biochrom, L2113, 1:20 in PBS). After the determination of the number of cells, the cells were suspended and the cells suspension was seeded into a 95-well microtitre plate (MTP; TPP, 92696) with a cell number of $3\times10^4$ cells/well.

The samples to be examined R1-R3 were diluted in medium and added to the cells at the corresponding concentrations. The plates were incubated for 72 h at 37° C. and 5% $CO_2$.

After the incubation period, the medium was removed and the cells were washed with PBS (phosphate-buffered saline, without $Mg^{2+}$ and $Ca^{2+}$; Biochrom, L1825).

For subsequent UV radiation, the cells were covered with 50 µl PBS per well and radiated at 1 $J/cm^2$+0.1 $J/cm^2$ and 2 $J/cm^2$ UVA+0.2 $J/cm^2$ UVB by means of a UV lamp simulating the natural spectrum of sunlight (Dr. Hönle, SOL 500).

After a further incubation of the cells at 37° C. and 5% $CO_2$ for 18 h, the sE-cadherin ELISA (R&D Systems, DCADE0) was carried out.

The microtitre plates were centrifuged at 250×g for 10 minutes and the media supernatants were carefully transferred to the microtitre plate coated with anti-sE-cadherin+assay diluent, without taking up the precipitated cell debris. The cell supernatants to be examined were incubated at room temperature for 2 hours while shaking. Subsequently, the plates were incubated with the $2^{nd}$ antibody (anti-sE-cadherin POD) at room temperature for 2 hours on the shaker. After the addition of the Glo reagent, a ten-minute incubation of the plate, protected from light, took place at room temperature.

Luminescence was measured in a microplate reader (Labsystems, Fluoscan Ascent Fla.). The obtained RLU values (Relative Luminescence Units) correspond to the content of interleukin-8 expressed. Cells that were not pretreated with R1, R2, R3 serve as control. The RLU values of these controls are set as 100% value.

The active agent complex of the invention (R3) significantly reduced the expression of E-cadherin fragment—sE-cadherin in a dose-dependent manner.

Figure 5:
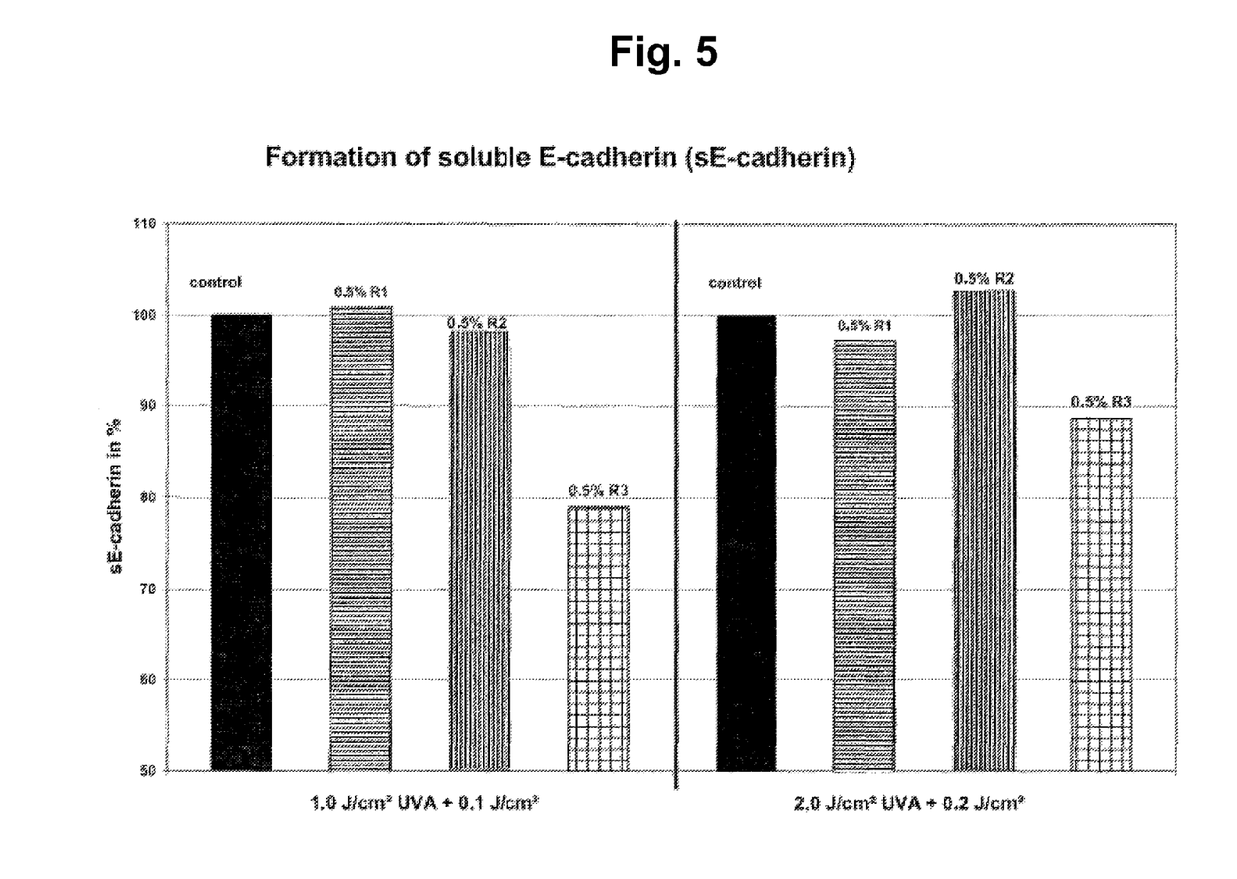
FIG. 5 showing the graphical presentation of formation of soluble E-Cadherein in human keratinocytes, pretreated with various active agent complexes, following ultraviolet radiation treatment at different UV dosages.

The individual components of the active agent complex, however, have, at best, an insignificant inhibitory effect (see also FIG. 5).

6. Impedance After UV Radiation

In order to evaluate epidermal integrity at cell level, the electrical cell-substrate impedance sensing method (ECIS) was used.

ECIS is a non-invasive method which allows to observe cell behaviour in real time and to make predictions regarding growth behaviour, cell adhesion, micro-movement of cells, morphological changes and, finally, barrier function properties.

This method is based on the finding that cells represent electrical resistance (impedance) and each change in volume, form and magnitude of the cell/cell contacts have a measurable effect on the impedance. This resistance is called impedance.

Healthy cells are seeded onto a chip on which they form a confluent monolayer over an electrode. After the formation of desmosomes and zonulae adherents (adherent junctions), it is possible to determine changes in impedance, which are not caused by a decrease in cell number but by morphological changes (cell-cell-contacts), by means of damages, e.g. damage by UV). This is possible by a real time observation period starting prior to the start of damage to several hours after completion of damage. Since, in case of moderate damage, it cannot be assumed that there are necrotic cells in the first minutes up to 1 hour (this would also be clear from the absence of regeneration and stable impedance values), the changes in the integrity of the cell layer (lawn) is clearly recognizable throughout this early observation period. Thus, this methodology is well suited to draw conclusions with respect to the integrity of the metabolically active layers of the epidermis. As the experimental results show, after an observation period of approximately 20 h with a radiation of 3 J, it can be clearly observed that the values of the cells treated with the individual components of the active agent complex are at the level of the control cells (R2) and significantly above (R1), respectively, (however, below the initial value). Surprisingly, cells that had been treated with the active agent complex of the invention showed values slightly above the initial value prior to radiation.

The high impedance loss of the control cells and of the cells treated with R1 and R2 may be explained by the possible initiation of apoptosis. Within a comparable period of time, this damage cannot be observed in the cells treated with the active agent complex. However, the enhancement of epidermal integrity is particularly clear during the first 30 minutes after the damage.

The control cells as well as the cells treated with the individual components R1 and R2 are almost at the same level, whereas the cells treated with the active agent complex of the invention (R3) were capable of maintaining a higher impedance level already during damaging.

Thus, with R3, the initial impedance value (100%) is reached again 30 minutes after UV radiation.

In contrast, control, R1 and R2 are still approximately 25% below the initial value at a comparable point in time.

Figure 6A:
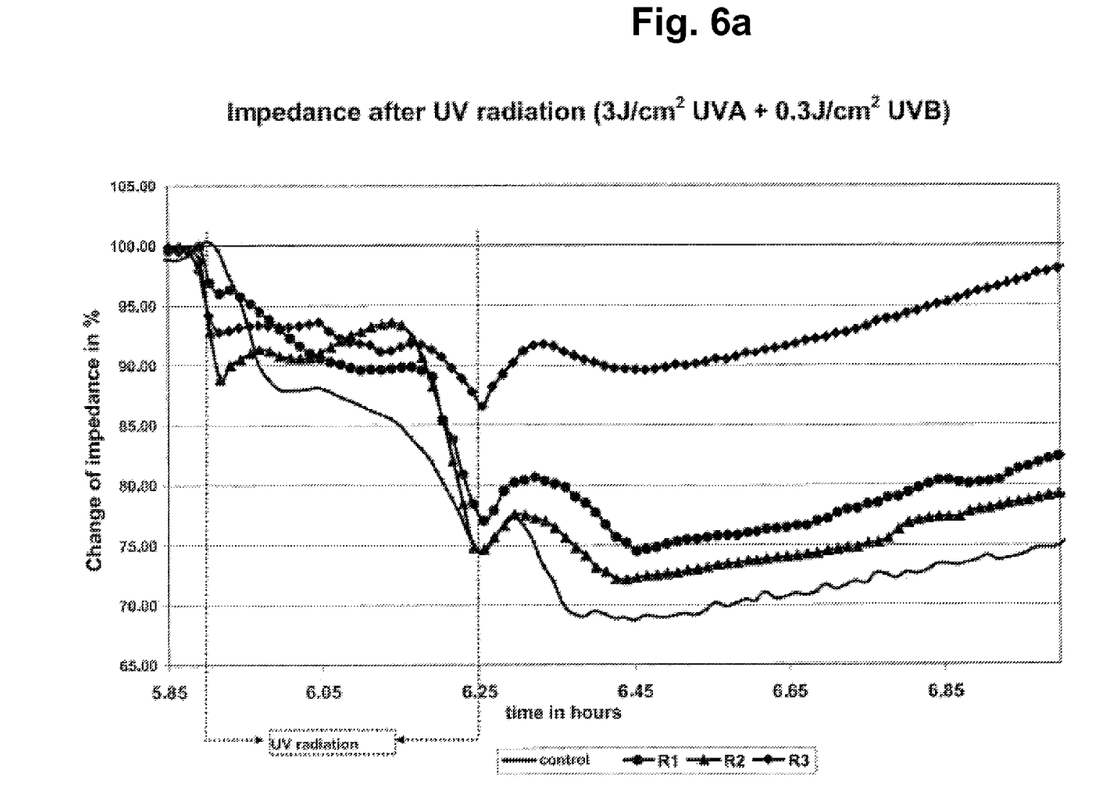
FIG. 6a showing the short term (within 1 h after UV irradiation) impedance change of human keratinocytes, pretreated with various active agent complexes, following ultraviolet radiation treatment. Initial impedance values were normalized to 100%.
Figure 6B:
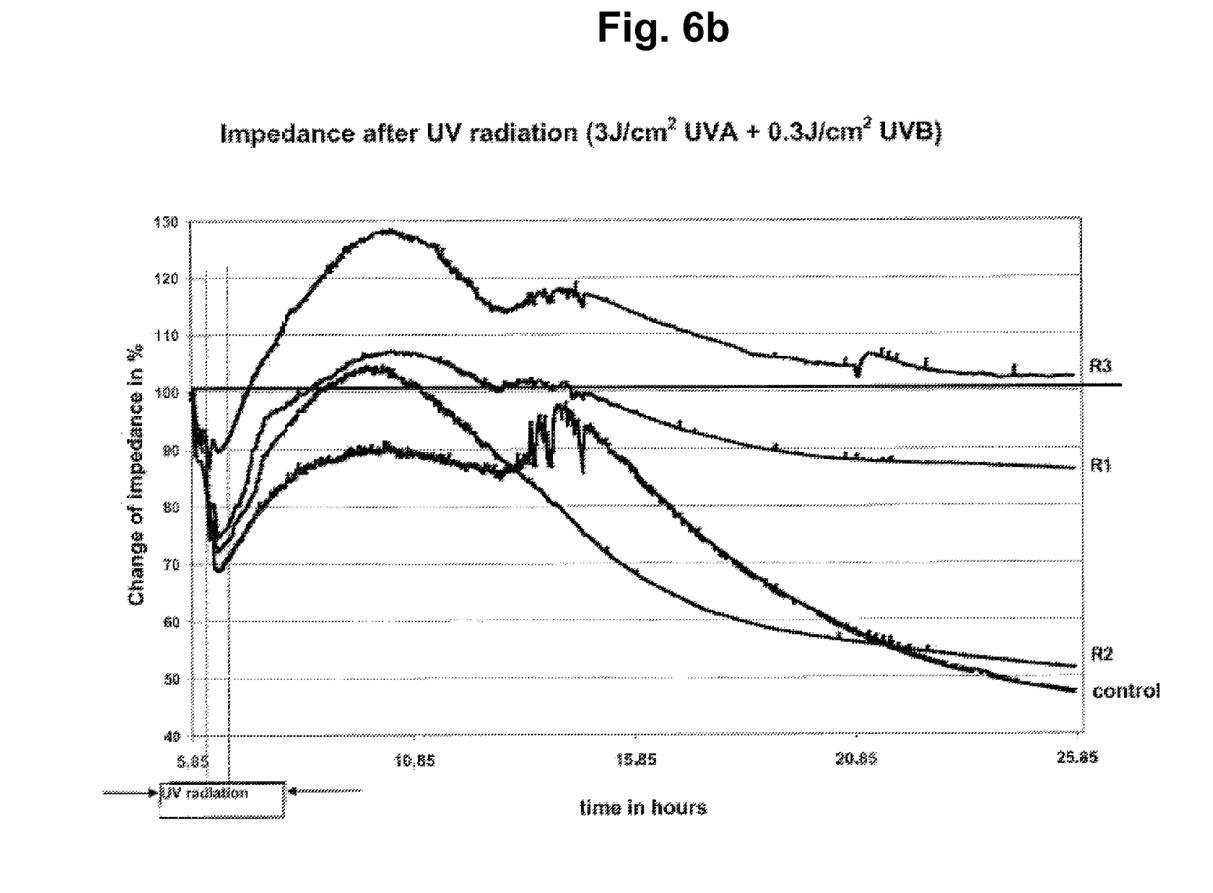
FIG. 6b showing the long term (20 h after UV irradiation) impedance change of human keratinocytes, pretreated with various active agent complexes, following ultraviolet radiation treatment. Initial impedance values were normalized to 100%.

The above results are evidence for the fact that the active agent complex of the invention (R3) is capable of significantly enhancing the epidermal integrity of the skin (see FIGS. 6a and 6b).

Impedance Measurement After UV Radiation—Procedure

Human keratinocytes were incubated at 37° C. and 5% $CO_2$ in Dulbecco's Modified Eagle Medium (DMEM; Biochrom, F0415) which was supplemented with 5% FCS (Fetal Calf Serum); Biochrom, S0115—heat-inactivated) and L-glutamine (Biochrom, K0282).

Prior to reaching the stationary growth phase, the cells were trypsinated which included a pretreatment with an EDTA-solution (ethylene diamine tetra-acetic acid; Biochrom, L2113, 1:20 in PBS). After the determination of the number of cells, the cells were suspended and the cells suspension was seeded onto an electrode chip (IBIDI, 8E 10) with a cell number of $3 \times 10^4$ cells/well.

The assays were incubated at 37° C. and 5% $CO_2$ for 72 h until a confluent monolayer was formed. Samples R1-R3 to be analysed were diluted at a concentration of 1.5% in medium without FCS for 24 h and added to the cells. After this period, the chip was connected to the ECIS measurement device. After a relatively constant impedance curve was reached (5 h), UV radiation at 3 $J/cm_2$ UVA+0.3 $J/cm_2$ UVB by means of a UV lamp simulating the natural spectrum of sunlight (Dr. Hönle, SOL 500) took place.

The chip was connected to the measurement device also during the radiation period so that a continuous registration of data was ensured. The data were registered for further 20 h.

7. Avoidance of Apoptotic Cells After UV Radiation

For the determination of apoptotic cells, a cytotoxicity test by Roche was used. This LDH test (Roche; 11644793) is based on the principle that the enzyme LDH (lactate dehydrogenase), which is present in the cytosol of intact cells, is discharged into the extracellular space (supernatant).

The emitted amount of LDH due to the cell's entry into apoptosis can be determined by means of this photometric test and is, thus, a measure for the present damage of the cell membrane and, thus, also for the number of apoptotic cells.

Human keratinocytes were incubated at 37° C. and 5% $CO_2$ in Dulbecco's Modified Eagle Medium (DMEM); Biochrom, F0415) which was supplemented with 5% FCS (Foetal Calf Serum; Biochrom, S 0115—heat-inactivated) and L-glutamine (Biochrom, K 0282).

Prior to reaching the stationary growth phase, the cells were trypsinated, which included pretreatment with an EDTA solution (ethylene diamine tetra-acetic acid, Biochrom, L2113, 1:20 in PBS). After determination of the number of cells, a cell suspension was prepared and seeded into a 96 well microtitre plate (MTP; TPP, 92696) with a cell number of $3 \times 10^4$ cells/well.

The samples to be examined, R1-R3, were diluted in medium and added to the cells at the corresponding concentrations. The plates were incubated for 72 h at 37° C. and 5% $CO_2$.

After expiry of this time period, the medium was removed and the cells were washed with PBS (phosphate buffered saline solution, without $Mg^{2+}$ and $Ca^{2+}$; Biochrom, L1825).

For the subsequent UV radiation, the cells were covered with 50 µl PBS/well and radiated with 1 $J/cm^2$ UVA+0.1 $J/cm^2$ UVB by means of a UV lamp simulating the natural sun light spectrum (Dr. Hönle, SOL 500).

After further incubation of the cells at 37° C. and 5% $CO_2$ for 18 h, the interleukin-8 luminescence ELISA was carried out (R&D Systems, Q8000B).

The microtitre plates were centrifuged at 250×g for 10 minutes and the media supernatants were carefully transferred to the new microtitre plate, without taking up the precipitated cell debris. After addition of the reaction mixture (diaphorase/NAD+iodine tetrazolium/sodium lactate), incubation of the plate for 30 minutes, protected from light, took place at room temperature.

Absorption was measured in a microplate reader (Fynex, MRX) at 480 nm, reference wavelength 630 nm. The OD values obtained correspond to the released amount of LDH enzyme and, thus, to the number of damaged and/or apoptotic cells. Cells which had not been pre-treated with R1, R2, R3 served as controls. The OD values of these control cells are fixed as 100% value.

The result of this test shows that both the treatment with the individual components and with the active agent complex according to the invention results in a reduction of apoptotic cells in comparison to the control cells.

With increased UV radiation dose, this result is still observable, even if the number of apoptotic cells on the whole has increased.

Figure 7:
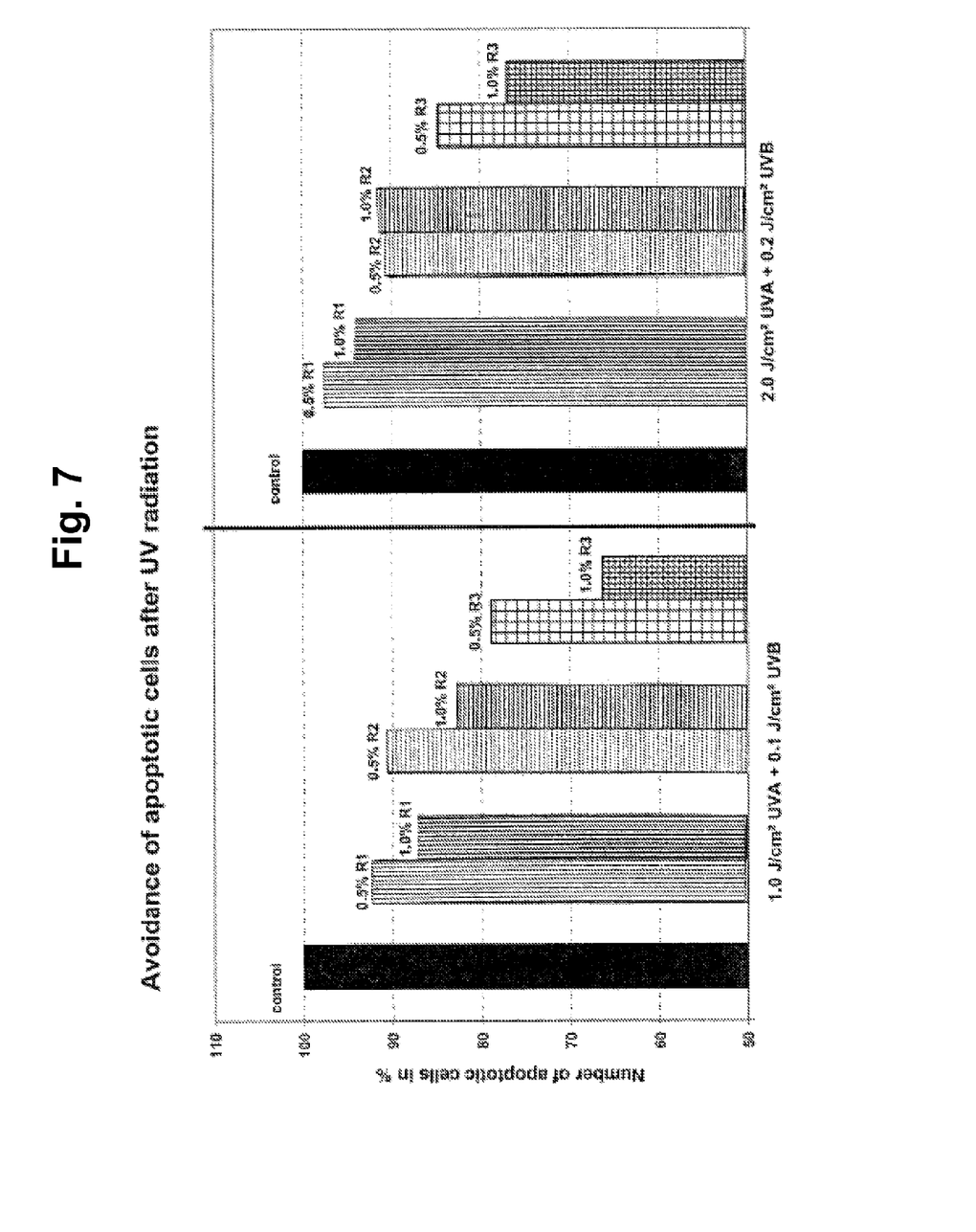
FIG. 7 showing the graphical presentation of prevention of apoptotic cells after ultraviolet radiation treatment at different UV dosages. Apoptotic cells were measured as LDH (Lactatedehydrogenase) which released by apoptotic cells. Human keratinocytes were pretreated with various active agent complexes.

In both experiments, however, the active agent complex according to the invention (R3) achieved a clearly better effect than the individual components (R1 and R2) alone, or the merely calculated addition of the result values of R1 and R2 (see also FIG. 7).

Thus, the active agent complex according to the invention from both extracts shows an overeffect with regard to the reduction of the expression of pro-inflammatory cytokines (IL-8, TNF-α) in various test models (osmotic stress, UV radiation, photoallergic reactions) and strengthening of the epidermal integrity, as could be determined due to the reduction of the E-cadherin degradation and a more rapid regeneration of the epidermal integrity. Due to its ability to protect the epidermal homeostasis in an effective manner in combination with its good tolerance, the active agent complex according to the invention is ideally suited to strengthen, maintain and restore the epidermal integrity.

The invention claimed is:

1. A composition comprising an active agent complex of extracts of *Poria cocos* and of a species of the genus *Phragmites* wherein the species of the genus *Phragmites* is selected from the group consisting of *Phragmities kharka* and *Phragmities communis*, and wherein the composition contains an effective amount of each and is between 1% (w/w) to 10% (w/w) of the active agent complex, and wherein the active agent complex is in the form of an emulsion, a stick, a foam or a gel.

2. The composition according to claim 1, wherein the species of the genus *Phragmites* is *Phragmites kharka*.

3. The composition according to claim 1, wherein the extracts comprise aqueous, glycolic or alcoholic extracts.

4. The composition according to claim 1 in form of a cream, an ointment, a paste, or a lotion.

5. The composition according to claim 1, wherein the composition contains between 2% (w/w) and 5% (w/w) active agent complex.

6. The composition according to claim 1, wherein the composition contains about 3% (w/w) active agent complex.

7. The composition according to claim 1, wherein the composition contains an effective amount of each between 1% (w/w) to 1.5% (w/w) of the active agent complex.

8. A topical application composition comprising an extract and one or more excipient(s), the extract consisting essentially of an active agent complex of extracts of *Poria cocos* and of, *Phragmites communis*, the active agent complex contains an effective amount of each and is between 1% (w/w) to 10% (w/w) of the active agent complex, wherein the composition is in the form of an emulsion, a stick, a foam or a gel.

9. The composition according to claim 8, wherein the composition contains an effective amount of each between 1% (w/w) to 1.5% (w/w) of the active agent complex.

10. A composition comprising an active agent complex of extracts of *Poria cocos* and of *Phragmites kharka*, wherein the active agent complex contains an effective amount of each and is between 1% (w/w) to 10% (w/w) of the active agent complex, wherein the composition is in the form of an emulsion, a stick, a foam or a gel.

11. The composition according to claim 10, wherein the extracts comprise aqueous, alcoholic or glycolic extracts.

12. The composition according to claim 10, wherein the active agent complex contains an effective amount of each and is between 1% (w/w) to 1.5% (w/w) of the active agent complex.

* * * * *